United States Patent [19]
Marrone et al.

[11] Patent Number: 6,077,506
[45] Date of Patent: *Jun. 20, 2000

[54] STRAIN OF BACILLUS FOR CONTROLLING PLANT DISEASE

[75] Inventors: Pamela Gail Marrone; Sherry D. Heins; Denise C. Manker, all of Davis; Desmond R. Jiménez, Woodland, all of Calif.; Chris N. Chilcott; Peter Wigley, both of Titirangi, New Zealand; Andrew Broadwell, Mt. Albert, New Zealand

[73] Assignees: AgraQuest, Inc., Davis, Calif.; BioDiscovery New Zealand Ltd., Titirangi, New Zealand

[ * ] Notice: This patent is subject to a terminal disclaimer.

[21] Appl. No.: 09/296,225

[22] Filed: Apr. 22, 1999

Related U.S. Application Data

[63] Continuation of application No. 08/789,334, Jan. 22, 1997, Pat. No. 5,919,447, which is a continuation of application No. 08/746,891, Nov. 18, 1996, abandoned.

[51] Int. Cl.$^7$ .................................................. A01N 63/00
[52] U.S. Cl. .................................... 424/93.461; 435/252.5
[58] Field of Search ...................... 435/252.5; 424/93.461

[56] References Cited

U.S. PATENT DOCUMENTS

| | | |
|---|---|---|
| 5,047,239 | 9/1991 | Pusey et al. |
| 5,049,379 | 9/1991 | Handelsman et al. |
| 5,061,495 | 10/1991 | Rossall |

FOREIGN PATENT DOCUMENTS

| | | |
|---|---|---|
| 48-032648 | 5/1973 | Japan . |
| 1144377 | 8/1985 | U.S.S.R. . |
| WO 94/09630 | 5/1994 | WIPO . |
| WO 95/24126 | 9/1995 | WIPO . |
| WO 96/08504 | 3/1996 | WIPO . |
| WO 96/39037 | 12/1996 | WIPO . |

OTHER PUBLICATIONS

Baker, et al., "Inhibitory effect of *Bacillus subtilis* on *Uromyces phaseoli* and on development of rust pustules on bean leaves" *Phytopathol.* 73:1148–1152 (1983).

Campbell, "*Biological Control of Microbial Plant Patogens*" Cambridge University Press, New York, p. 77 (1989).

Ferreira et al., "Biological control of *Eutypa lata* on grapevine by an antagonistic strain of *Bacillus subtilis*" *Phytopathol.* 81:283–287 (1991).

He et al., "Zwittermicin A, an antifungal and plant protection agent from *Bacillus cereus*" *Tetra. Lett.* 35:2499–2502 (1994).

Liefert et al., "Antibiotic production and biocontrol activity by *Bacillus subtilis* CL27 and *Bacillus pumilus* CL45" *J. Appl. Bacteriol.* 78:79–108 (1985).

McKeen et al., "Production and partial characterization of antifungal substaces antagonistic to *Monilinia fructicola* from *Bacillus subtilis* " *Phytophathol.* 76:136–139 (1986).

Milner et al., "Production of Kanosamine by *Bacillus cereus* UW85" *Appl. Environ. Microbiol.* 62:3061–3065 (1996).

Osburn et al., "Effect of *Bacillus cereus* UW85 on the yield of soybean at two field sites in Wisconsin" *Am. Phytophathol. Soc.* 79:551–556 (1995).

Pusey et al., "Pilot tests for commercial production and application of *Bacillus Subtilis* (B–3) for postharvest control of peach brown rot" *Plant Disease* 72:622–626 (1988).

Schwinn et al., "Control with Chemicals" in: Advances in Plant Pathology: Phytophthora Infestans, The Cause of Late Blight of Potato, vol. 7, Aademic Press, San Diego, CA, p. 244 (1991).

Sholberg et al., "Biocontrol of postharvest diseases of apple using *Bacillus* spp. isolated from stored apples" *Can. J. Microbiol.* 41:247–252 (1995).

Singh et al., "*Bacillus subtilis* as a control agent against fungal pathogens of citrus fruit" *Trans. Br. mycol. Soc.* 83:487–490 (1984).

Smith et al., "Suppression of cottony leak of cucumber with *Bacillus Cereus* strain UW85" *Plant Disease* 77:139–142 (1993).

Stabb et al., "Zwittermicin A–producing strains of *Bacillus cereus* from diverse soil" *Appl. Environ. Microbiol.* 60:4404–4412 (1994).

Stanbury et al., "Principles of Fermentation Technology" Pergamon Press, Oxford, p. 26–37 (1984).

Swinburne et al., "Production of antibiotics by *Bacillus subtilis* and their effect on fungal colonists of apple leaf scars" *Trans. Br. mycol. Soc.* 65:211–217 (1975).

*Primary Examiner*—Irene Marx
*Attorney, Agent, or Firm*—Antoinette F. Konski; Baker & McKenzie

[57] ABSTRACT

The present invention provides a novel *Bacillus thuringiensis* strain that exhibits broad antifungal and antibacterial activity. The invention also provides the use of the *Bacillus thuringiensis* strain or the antibiotic produced by the strain for control of a broad range of fungal and bacterial plant pathogens.

21 Claims, 3 Drawing Sheets

STRAIN OF BACILLUS FOR CONTROLLING PLANT DISEASE

This application is a continuation of U.S. Ser. No. 08/789,334, filed Jan. 22, 1997, now U.S. Pat. No. 5,919,447, filed Jan. 22, 1997, which in turn is a continuation of U.S. Ser. No. 08/746,891, filed Nov. 18, 1996, now abandoned, the contents of which are hereby incorporated by reference into the present disclosure.

TECHNICAL FIELD OF THE INVENTION

The present invention is in the field of biopesticides. More particularly this invention relates to the finding that a novel strain of Bacillus thuringiensis, AQ52, can inhibit a broad range of fungal and bacterial plant diseases. The invention also relates to fungicidal and bactericidal compositions comprising this novel Bacillus strain and the antibiotic produced by this strain either alone, or in combination with other chemical and biological pesticides.

BACKGROUND OF THE INVENTION

For a number of years, it has been known that various microorganisms exhibit biological activity useful in controlling plant diseases. Although progress has been made in the field of identifying and developing biological pesticides for controlling various plant diseases of agronomic and horticultural importance, most of the pesticides in use are still synthetic compounds. Many of these chemical fungicides are classified as carcinogens by the EPA and are toxic to wildlife and other non-target species. In addition, pathogens may develop resistance to chemical pesticides (see, e.g., Schwinn et al., p. 244, ADVANCES IN PLANT PATHOLOGY: PHYTOPHTHORA INFESTANS, THE CAUSE OF LATE BLIGHT OF POTATO (Academic Press, San Diego 1991).

Biological control offers an attractive alternative to synthetic chemical fungicides. Biopesticides (living organisms and the naturally produced compounds produced by these organisms) can be safer, more biodegradable, and less expensive to develop.

Screening programs have identified certain Bacillus sp. (B. sp. includes B. subtilis, B. cereus, B. mycoides, B. anthracis and B. thuringiensis) strains which exhibit antifungal activity. (See, e.g., Statt et al. (1990) Applied Environ. Microbiol. 60(12):4404–4412). These strains have been shown to produce zwittermicin-A and/or antibiotic B (now known as kanosamine (Milner et al. (1996) Appl. Environ. Microb. 62:3061–3056)), two antibiotic agents which are effective against the soil borne disease "damping-off" caused by Phytophthora medicaginis, Phytophthora nicotianae, Phytophthora aphanidermatum or Sclerotinia minior. (See, Stabb et al., supra). Zwittermicin-A is a water-soluble, acid-stable linear aminopolyol molecule. (see, He et al. (1994) Tetra. Lett. 35(16):2499–2502).

U.S. Pat. No. 5,049,379 to Handelsman et al. describes how zwittermicin A-producing B. cereus can be used to control the below-ground seedling diseases "root rot" and "damping off" in alfalfa and soybean. When the seed is coated with zwittermicin-A produced by B. cereus ATCC 53522, the pathogenic activity of the root rot fungus is inhibited. Similarly, application of spore-based formulations of certain B. cereus strains to soybean seeds or the soil surrounding the seeds; has been shown to improve soybean yield at field sites. (See, Osburne et al. (1995) Am. Phytophathol. Soc. 79(6): 551–556). Methods of applying biopesticides are well known in the art and include, for example, wettable powders, dry flowables, microencapsulation of effective agents, liquid or solid formulations and antibiotic fractions obtained from suitable cultures. (See, e.g., U.S. Pat. No. 5,061,495 to Rossall or U.S. Pat. No. 5,049,379 to Handelsman).

Smith et al. (1993) Plant Disease 77(2):139–142 report that the activity of the soil-borne fungus, Pythium aphanidermatum, that causes cottony cucumber leak can be suppressed using zwittermicin-producing B. cereus strain UW85. Liefert et al. (1995) J. Appl. Bacteriol. 78:97–108 report the production of anti-Botrytis and anti-Alternaria brassicicola antibiotics by two Bacillus strains, B. subtilis CL27 and B. pumilis CL45. The whole broth and cell-free filtrates were active against Botrytis and Alternaria in vitro tests and were active against Botrytis in in vivo small plants tests on Astilbe.

Sholberg et al. (1995) Can. J Microbiol. 41:247–252, Swinburne et al, (1975) Trans. Brit. Mycol Soc. 65:211–217, Singh and Deferral (1984) Trans. Br. Mycol Soc. 83:487490, and Ferreira, et al. (1991) Phytopathology 81:28–287 disclose the use of Bacillus sp. and Bacillus subtilis as biocontrol agents of fungal plant pathogens. Baker et al. (1983) Phytopathology 73:1148–1152 also report on an antifungal Bacillus subtilis for use on plant pathogens. Pusey et al. (1988) Plant Dis. 72:622–626, Pusey and Robins (U.S. Pat. No. 5,047,239) and McKeen et al. (1986) Phytopathol. 76:136–139 disclose control of post harvest fruit rot using B. subtilis. McKeen et al., supra, have shown that antibiotics similar to the low molecular weight iturin cyclic polypeptides contribute to this fungicidal activity of B. subtilis.

Stabb et al. (1990) tested 11 Bacillus thuringiensis strains for zwittermicin production. Only one strain (BGSC4F1) tested positive for zwittermicin. This strain was weakly active against alfalfa damping off. There are no reports, however, of strains of Bacillus thuringiensis with broad fungicidal and bactericidal activity.

DISCLOSURE OF THE INVENTION

A novel antibiotic-producing strain of Bacillus thuringiensis is provided that exhibits broad fungicidal and bactericidal activity. Also provided are methods of treating or protecting plants from fungal and bacterial infections comprising the step of applying an effective amount of the novel antibiotic-producing strain of Bacillus thuringiensis, AQ52, the antibiotic produced by the novel bacterial strain, or combinations thereof. In addition, at least one other antibiotic-producing microorganism or biological or chemical pesticide can be combined with the novel bacterial strain and/or antibiotic of the present invention. The novel Bacillus thuringiensis strain, AQ52, can be provided as a suspension in a whole broth culture or as an antibiotic-containing supernatant obtained from a whole broth culture of the bacterial strain.

MODES OF CARRYING OUT THE INVENTION

The present invention provides a novel strain of Bacillus thuringiensis which, unlike previously described Bacillus sp., exhibits broad antifungal and antibacterial activity. This novel strain is designated AQ52 and was deposited at the Agricultural Research Culture Collection (NRRL), International Depositary Authority, 1815 N. University Street, Peoria, Ill. 61604 USA, on Aug. 28th, 1996 under the provisions of the Budapest Treaty on the International Recognition of the Deposit of Microorganisms for the Purpose of Pat. Procedure under Accession No. B21619. The invention also includes methods of treating or preventing fungal and bacterial diseases in plants using the novel bacterial strain or antibiotic-containing supernatants or purified antibiotic obtained from the novel bacterial strain. In addition, at least one other antibiotic-producing microorganism or biological or chemical pesticide can be combined with the novel bacterial strain and/or antibiotic of the present invention.

Definitions

As used herein, "biological control" is defined as control of a pathogen by the use of a second organism. Known mechanisms of biological control include enteric bacteria which control root rot by out-competing fungi for space on the surface of the root. Bacterial toxins, such as antibiotics, have been used to control pathogens. The toxin can be isolated and applied directly to the plant or the bacterial species may be administered so it produces the toxin in situ.

The term "fungus" or "fungi" includes a wide variety of nucleated, sporebearing organisms which are devoid of chlorophyll. Examples of fungi include yeasts, mildews, molds, rusts, and mushrooms.

The term "bacteria" includes any prokaryotic organism that does not have a distinct nucleus.

"Fungicidal" means the ability of a substance to increase mortality or inhibit the growth rate of fungi.

"Antibiotic" includes any substance which is able to inhibit or kill a microorganism. Antibiotics may be produced by a microorganism or by a synthetic or semisynthetic process. The term, therefore, includes a substance which inhibits or kills fungi, for example, zwittermicin-A or kanosamine. "Antifungal" includes any substance which is able to kill or inhibit the growth of fungi.

The term "culturing" refers to the propagation of organisms on or in media of various kinds. "Whole broth culture" refers to a liquid culture containing both cells and media. "Supernatant" refers to the liquid broth remaining when cells grown in broth are removed by centrifugation, filtration, sedimentation or other means well known in the art.

An "effective amount" is an amount sufficient to effect beneficial or desired results. An effective amount can be administered in one or more administrations. In terms of treatment and protection, an "effective amount" is that amount sufficient to palliate, ameliorate, stabilize, reverse, slow or delay the progression of fungal or bacterial disease states.

We describe a novel strain of Bacillus thuringiensis that has broad antifungal and antibacterial activity. We have shown that this strain (AQ52) produces zwittermicin. This is the first reported zwittermicin-producing Bacillus thuringiensis strain to exhibit broad antifungal and antibacterial activity.

In another aspect, the present invention provides a method of treating or protecting plants from fungal and bacterial infections comprising applying an effective amount of a supernatant obtained from a whole broth culture of Bacillus thuringiensis AQ52 within the present invention. The supernatant may be obtained by means well known in the art including centrifugation, filtration, sedimentation or the like.

In another aspect, the invention encompasses a method of treating or protecting plants from fungal and bacterial infections comprising applying an effective amount of the novel strain of Bacillus thuringiensis as a whole broth culture.

In a further aspect, the invention encompasses a method of treating, or protecting plants from fungal and bacterial diseases comprising applying an effective amount of the antibiotic produced by the novel strain of Bacillus thuringiensis.

In order to achieve good dispersion and adhesion of compositions within the present invention, it may be advantageous to formulate the whole broth culture, supernatant and/or the antibiotic with components that aid dispersion and adhesion. Suitable formulations will be known to those skilled in the art Compositions within the present invention can be formulated as wettable powders, granules and the like, or can be microencapsulated in a suitable medium, and the like. Examples of other formulations include, but are not limited to, soluble powders, wettable granules, dry flowables, aqueous flowables, wettable dispersible granules, emulsifiable concentrates and aqueous suspensions. Other suitable formulations will be known to those skilled in the art.

All patents and publications cited herein are incorporated by reference.

The following examples are provided to illustrate the invention. These examples are not to be construed as limiting.

EXAMPLES

Example 1

Characterization of Strain AQ52

Confirmation of Identification of AQ52 as Bacillus thuringiensis

Isolates were identified based on whole-cell cellular fatty acids, derivatized to methyl esters (FAMEs) as described in Miller, L. T. (1982) J. Clin. Microbiol. 16:584–586. Gas chromatography was performed using the MIDI system (Microbial Identification System, Inc., Newark, Del. The procedure and protocols used for growing the bacterial cultures and instrument specification are described by MIDI (Identification of bacteria by gas chromatography of cellular fatty acids. Technical Note # 101. MIDI Inc., 115 Barksdale Professional Center, Newark, Del.). Isolates were grown on TSA (BBL) plates at 28° C. and cells were harvested after 24 hours. One mL of a methanolic NaOH (15% [wt/vol] NaOH in 50% [vol/vol] methanol) was added and cells were saponified at 100° C. for 30 minutes.

Esterification of fatty acids was performed using 2 mLs of 3.25 N FrCl in 46% (vol/vol) methanol at 80° C. for 10 minutes. The FAMEs were extracted into 1.25 mL of 1:1 (vol/vol) methyl-tert-butyl ether-hexane, and the organic extract washed with 3 mL of 1.2% (wt/vol) NaOH before analysis by gas chromatography. The GC (Hewlett-Packard 5890A) was equipped with a flame ionization detector and capillary column (Hewlett-Packard no. 19091B-102 (Crosslinked 5% phenyl-methyl silicone; 25m×0.22 nm ID; film thickness, 0.33 µm; phase ratio, 150) with hydrogen as the carrier gas. FAME peaks were automatically integrated by a Hewlett-Packard 3392 integrator and bacterial isolates named using the MIDI Microbial Identification Software (Sherlock TSBA Library version 3.80). The FAME profile of Xanthomonas maltophila ATCC 13637 was used as reference check for the MIDI determinations.

The results of the three separate runs of the MIDI profile identified AQ52 as a Bacillus thuringiensis. The similarity index scores are as follows:

run 1: 0.180, *Bacillus thuringiensis*
run 2: 0.177, *Bacillus thuringiensis*
run 3: 0.159, *Bacillus thuringiensis*

Figure 1:
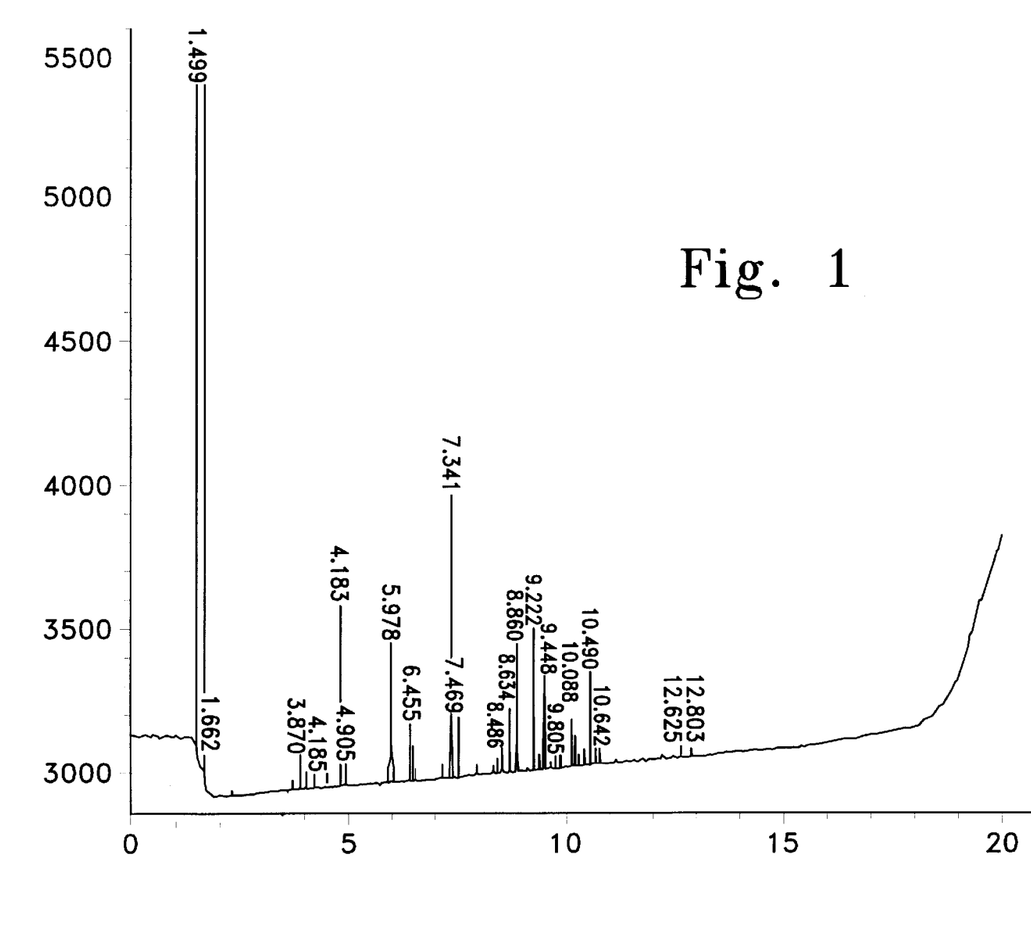
FIGS. 1, 2 and 3 show three gas chromatography spectra of strain AQ52 whole-cell cellular fatty acids, derivatized to methyl esters (FAMEs) using MIDI chromatography. Corresponding tabular results are found in Tables 1, 2 and 3, respectively.
Figure 2:
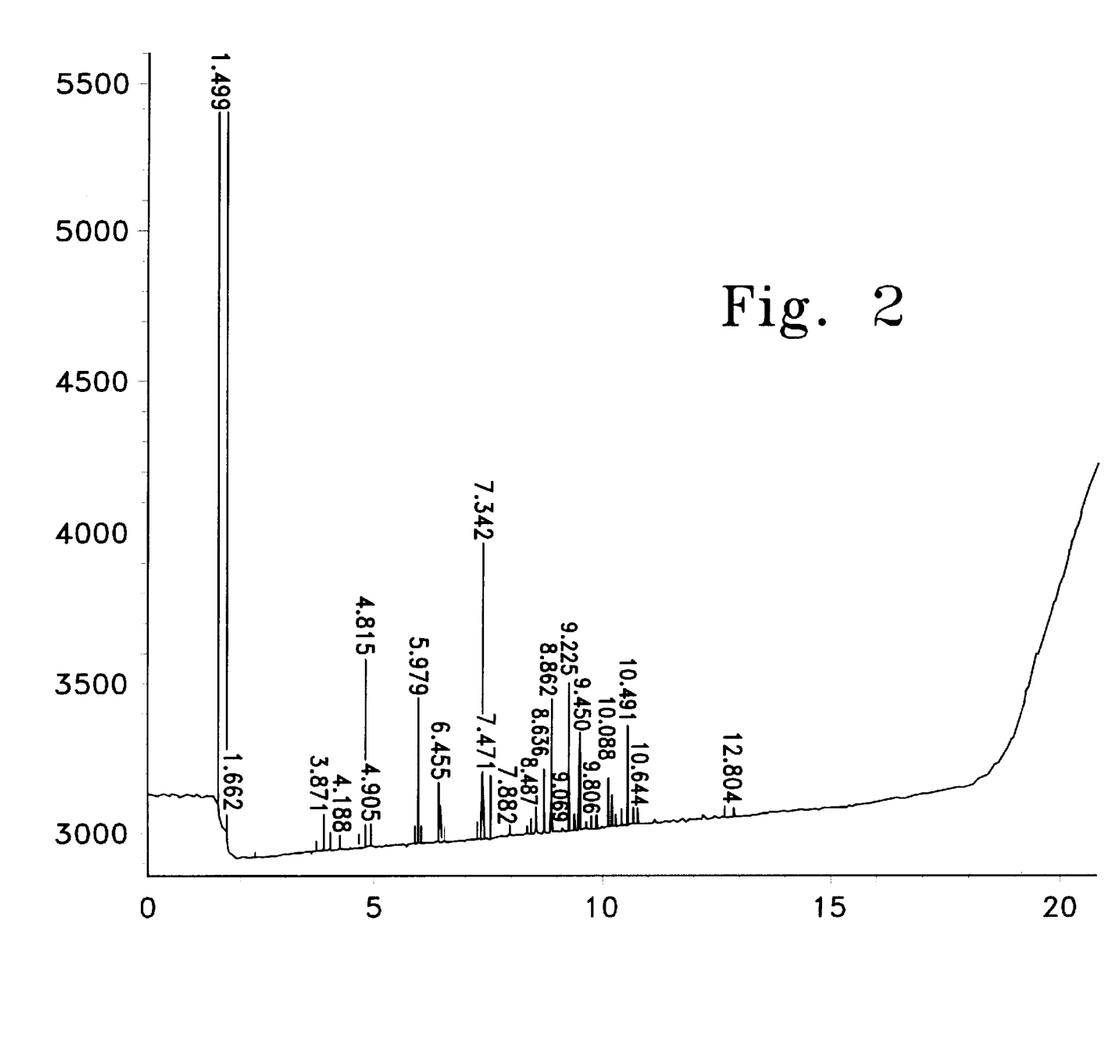
Figure 3:
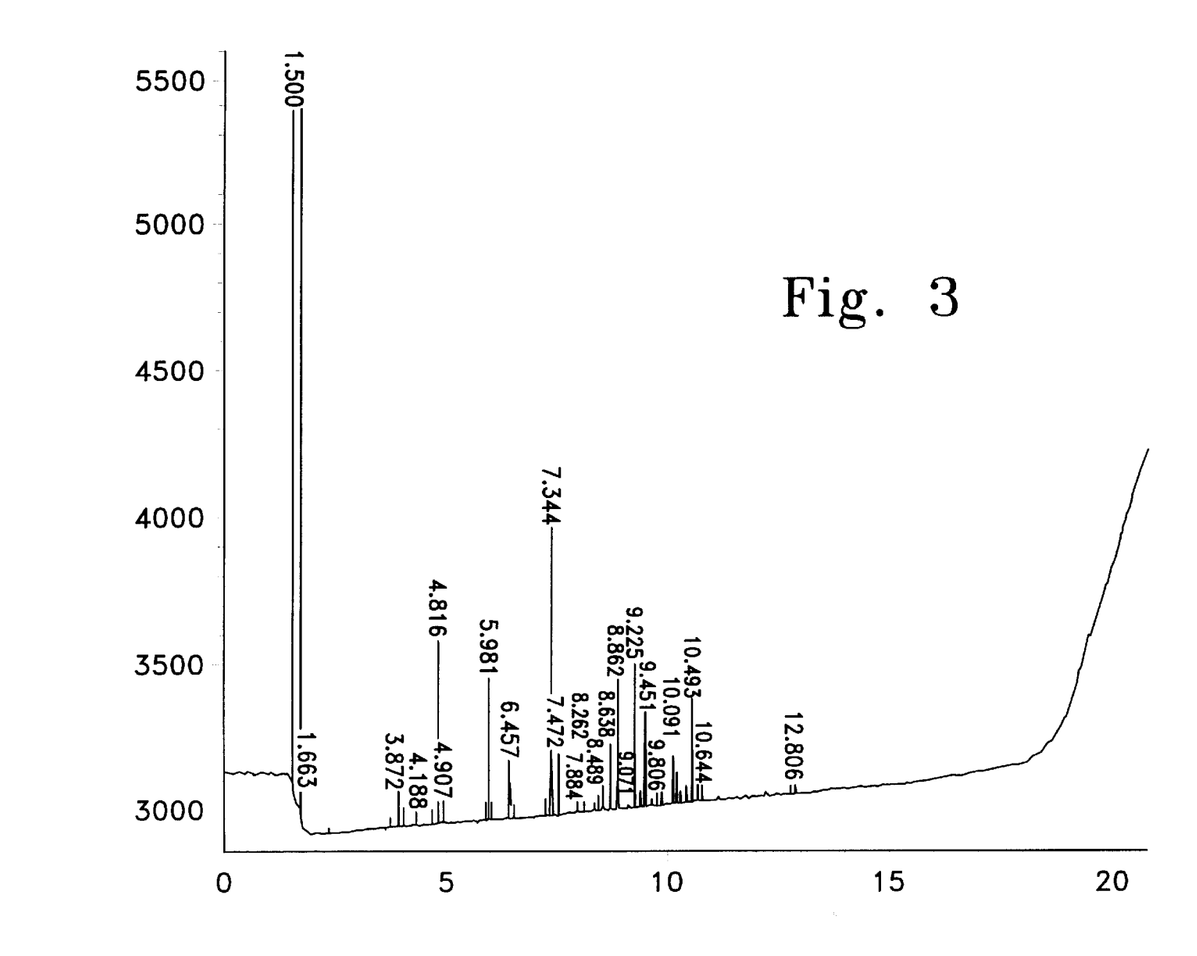

The actual MIDI profiles of the strain are shown in FIGS. 1, 2, 3 and in Tables 1, 2 and 3.

In addition to being characterized by FAME profiles, isolates were assessed for carbon substrate utilization using the Biolog microplate panel (Biolog, Inc., Hayward, Calif.) as described in Bochner (1989) *Nature* 339:157–158. The Biolog microplate is comprised of prefilled and dried panel wells with 95 different carbon substrates (plates are available for gram-positive and gram negative bacteria). Isolates were grown in liquid medium at 28° C. and after 24 hours a washed cell suspension (0.%85 saline) was inoculated into each panel well of a GP MicroPlate (Biolog, Inc). After 24 hours at 28° C., carbon utilization reactions were assessed. Substrate utilization profiles were then compared to the Biolog Gram-Positive Data Base (release 3.50) and isolated matched to closest similar species.

Biolog results give a similarity index of 0.612 positive identification as *Bacillus thuringiensis*.

TABLE 1

Gas Chromatography of AQ52

Sherlock Version 1.06 DATA: C96A02775A 03-OCT-96 13:44:43
ID: 2902　　AGRAQUEST-52 REP 1　　　　　　　　　　　　　　　　　　Date of run: 03-OCT-96 13:19:34
Bottle: 16　　SAMPLE (ARROBE)

| RT | Area | Ar/Rt | Respon | ECL | Name | % | Comment 1 | | Comment 2 | |
|---|---|---|---|---|---|---|---|---|---|---|
| 1.499 | 358849200 | 0.024 | — | 7.025 | SOLVENT PEAK | — | <min rt | | | |
| 1.622 | 738 | 0.022 | — | 7.403 | — | — | <min rt | | | |
| 3.870 | 1206 | 0.029 | 1.123 | 11.608 | 12:0 ISO | 2.06 | *deviates | 0.000 | Ref | 0.000 |
| 4.185 | 522 | 0.035 | 1.098 | 12.000 | 12:0 | 0.87 | *deviates | 0.000 | Ref | 0.000 |
| 4.813 | 6324 | 0.028 | 1.063 | 12.612 | 13:0 | 10.22 | *deviates | −0.000 | Ref | −0.001 |
| 4.905 | 972 | 0.028 | 1.058 | 12.701 | 13:0 ANTEISO | 1.56 | *deviates | 0.000 | Ref | 0.000 |
| 5.978 | 5574 | 0.031 | 1.014 | 13.617 | 14:0 ISO | 8.59 | *deviates | −0.001 | Ref | −0.002 |
| 6.455 | 2574 | 0.034 | 0.997 | 14.001 | 14:0 | 3.90 | *deviates | 0.001 | Ref | 0.000 |
| 7.341 | 12882 | 0.035 | 0.974 | 14.622 | 15:0 ISO | 19.07 | *deviates | 0.001 | Ref | −0.000 |
| 7.469 | 2292 | 0.035 | 0.970 | 14.71 1 | 15:0 ANTEISO | 4.31 | *deviates | 0.000 | Ref | −0.000 |
| 8.486 | 1320 | 0.039 | 0.948 | 15.386 | 16:1 w7c alcohol | 1.90 | *deviates | 0.000 | | |
| 8.634 | 2298 | 0.039 | 0.946 | 15.481 | Sum In Feature 3 | 3.30 | *deviates | −0.001 | 16:1 ISO I/14:0 30 | |
| 8.860 | 6612 | 0.042 | 0.941 | 15.625 | 16:0 ISO | 9.46 | *deviates | −0.001 | Ref | −0.002 |
| 9.222 | 7080 | 0.040 | 0.935 | 15.856 | Sum In Feature 4 | 10.06 | *deviates | −0.000 | 16:1 w7t/15i20H | |
| 9.448 | 4746 | 0.039 | 0.931 | 16.000 | 16:0 | 6.72 | *deviates | 0.000 | Ref | −0.001 |
| 9.805 | 726 | 0.037 | 0.926 | 16.216 | 15:0 20H | 1.02 | *deviates | −0.001 | | |
| 10.088 | 2574 | 0.044 | 0.922 | 16.387 | ISO 17:1 w10C | 3.61 | *deviates | −0.000 | | |
| 10.209 | 1956 | 0.044 | 0.920 | 16.460 | ISO 17:1 w5c | 2.74 | *deviates | −0.001 | | |
| 10.345 | 546 | 0.040 | 0.918 | 16.542 | 17:1 ANTEISO 1 | 0.76 | *deviates | 0.001 | | |
| 10.490 | 4812 | 0.040 | 0.916 | 16.630 | 17:0 ISO | 6.70 | *deviates | 0.001 | Ref | 0.000 |
| 10.642 | 942 | 0.041 | 0.914 | 16.722 | 17:0 ANTEISO | 1.31 | *deviates | −0.000 | Ref | −0.001 |
| 12.605 | 2874 | 0.086 | — | 17.883 | — | — | | | | |
| 12.625 | 2896 | 0.101 | — | 17.895 | — | — | >max ar/ht | | | |
| 12.803 | 1350 | 0.063 | 0.889 | 18.000 | 18:0 | 1.82 | *deviates | −0.000 | Ref | −0.001 |
| ****** | 2298 | — | — | — | Summed Feature 3 | 3.30 | 12:0 ALDE ? | | unknown 10.928 | |
| ****** | — | — | — | — | — | — | 16:1 ISO I/14:0 30H | | 14:0 30H/16:1 ISO I | |
| ****** | 7080 | — | — | — | Summed Feature 4 | 10.06 | 15:0 ISO 20H/16:1w7t | | 16:1 w7t/15i20H | |

*ECL
| Solvent Ar | Total Area | | Named Area | % Named | | Total Amnt | Nbr Rev | ECL Deviation | Ref ECL Shift | |
|---|---|---|---|---|---|---|---|---|---|---|
| 358849200 | 73710 | | 67938 | 92.17 | | 65776 | 13 | 0.001 | 0.001 | |

| TSBA | [Rev 3.80)] | Bacillus | 0.180 | (*Bacillus cereus* group) |
|---|---|---|---|---|
| | | *B. thuringiensis* | 0.180 | (*Bacillus cereus* group) |
| | | *B. cereus**　 | 0.112 | |
| CLIN | [Rev 3.80] | *NO MATCH* | | |
| RHI %-1 | [Rev 1.0] | *NO MATCH* | | |

TABLE 2

Gas Chromatography of AQ52

Sherlock Version 1.06 DATA: C96A02775A 03-OCT-96 14:10:00
ID: 2903　　AGRAQUEST-52 REP 2　　　　　　　　　　　　　　　　　　Date of run: 03-OCT-96 13:45:04
Bottle: 17　　SAMPLE (ARROBE)

| RT | Area | Ar/Rt | Respon | ECL | Name | % | Comment 1 | Comment 2 |
|---|---|---|---|---|---|---|---|---|
| 1.499 | 356971800 | 0.024 | — | 7.023 | SOLVENT PEAK | — | <min rt | — |
| 1.622 | 990 | 0.023 | — | 7.401 | — | — | <min rt | |

TABLE 2-continued

Gas Chromatography of AQ52

| | | | | | | | | | | |
|---|---|---|---|---|---|---|---|---|---|---|
| 3.871 | 1140 | 0.026 | 1.123 | 11.608 | 12:0 ISO | 1.86 | *deviates | −0.000 | Ref | 0.001 |
| 4.188 | 618 | 0.035 | 1.098 | 12.001 | 12:0 | 0.98 | *deviates | 0.001 | Ref | 0.003 |
| 4.815 | 6738 | 0.028 | 1.063 | 12.612 | 13:0 | 10.39 | *deviates | 0.000 | Ref | 0.001 |
| 4.905 | 1008 | 0.029 | 1.058 | 12.700 | 13:0 ANTEISO | 1.56 | *deviates | −0.001 | Ref | 0.000 |
| 5.979 | 5796 | 0.032 | 1.014 | 13.616 | 14:0 ISO | 8.52 | *deviates | −0.002 | Ref | −0.001 |
| 6.455 | 2628 | 0.034 | 0.997 | 14.000 | 14:0 | 3.80 | *deviates | −0.000 | Ref | 0.000 |
| 7.342 | 13062 | 0.034 | 0.974 | 14.621 | 15:0 ISO | 10.44 | *deviates | 0.000 | Ref | 0.001 |
| 7.471 | 3030 | 0.035 | 0.970 | 14.712 | 15:0 ANTEISO | 4.26 | *deviates | 0.001 | Ref | 0.001 |
| 7.882 | 576 | 0.041 | 0.961 | 15.000 | 15:0 | 0.80 | *deviates | −0.000 | Ref | 0.000 |
| 8.487 | 1356 | 0.037 | 0.948 | 15.386 | 16:1 w7c alcohol | 1.87 | *deviates | 0.001 | | |
| 8.636 | 2502 | 0.037 | 0.946 | 15.481 | Sum In Feature 3 | 3.43 | *deviates | −0.001 | 16:1 ISO I/14:0 30H | |
| 8.862 | 7038 | 0.041 | 0.941 | I5.625 | 16:0 ISO | 9.61 | *deviates | −0.000 | Ref | −0.001 |
| 9.069 | 570 | 0.042 | 0.938 | 15.758 | 16:0 w11c | 0.78 | *deviates | 0.001 | | |
| 9.225 | 7362 | 0.039 | 0.935 | 15.857 | Sum In Feature 4 | 9.98 | *deviates | 0.001 | 16:1 w7t/15i20H | |
| 9.450 | 4992 | 0.039 | 0.931 | 16.001 | 16:0 | 6.74 | *deviates | 0.001 | Ref | 0.001 |
| 9.806 | 870 | 0.045 | 0.926 | 16.216 | 15:0 20E | 1.17 | *deviates | −0.001 | | |
| 10.088 | 2496 | 0.039 | 0.922 | 16.386 | ISO 17:1 w10c | 3.34 | *deviates | −0.001 | | |
| 10.210 | 2040 | 0.044 | 0.920 | 16.460 | ISO 17:1 w5c | 2.72 | *deviates | −0.001 | | |
| 10.343 | 588 | 0.041 | 0.918 | 16.540 | 17:1 ANTEISO A | 0.78 | *deviates | −0.001 | | |
| 10.491 | 5226 | 0.038 | 0.916 | 16.630 | 17:0 ISO | 6.94 | *deviates | 0.001 | Ref | 0.001 |
| 10.644 | 894 | 0.040 | 0.914 | 16.722 | 17:0 ANTEISO | 1.18 | *deviates | 0.000 | Ref | 0.000 |
| 12.804 | 654 | 0.045 | 0.889 | 17.999 | 18:0 | 0.84 | *deviates | −0.001 | Ref | −0.001 |
| ****** | 2298 | — | — | — | Summed Feature 3 | 3.43 | 12:0 ALDE? | | unknown 10.928 | |
| ****** | — | — | — | — | — | — | 16:1 ISO I/14:0 30H | | 14:0 30H/16:1 ISO I | |
| ****** | 7080 | — | — | — | Summed Feature 4 | 9.98 | 15:0 ISO 20H/16:1w7t | | 16:1 w7t/15i20H | |

| *ECL Solvent Ar | Total Area | | Named Area | % Named | | Total Amnt | Nbr Rev | ECL Deviation | Ref ECL Shift | |
|---|---|---|---|---|---|---|---|---|---|---|
| 356971800 | 71184 | | 71184 | 100.00 | | 68947 | 14 | 0.001 | 0.001 | |

| TSBA | [Rev 3.80)] | Bacillus | 0.177 | (*Bacillus cereus* group) |
|---|---|---|---|---|
| | | B. thuringiensis | 0.177 | (*Bacillus cereus* group) |
| | | B. cereus* | 0.112 | |
| CLIN | [Rev 3.80] | *NO MATCH* | | |
| RHI %-1 | [Rev 1.0] | *NO MATCH* | | |

TABLE 3

Gas Chromatography of AQ52

Sherlock Version 1.06 DATA: C96A02775A 03-OCT-96 14:35:22
ID: 2904   AGRAQUEST-52 REP 3                                Date of run: 03-OCT-96 14:10:20
Bottle: 18   SAMPLE (ARROBE)

| RT | Area | Ar/Rt | Respon | ECL | Name | % | Comment 1 | | Comment 2 | |
|---|---|---|---|---|---|---|---|---|---|---|
| 1.500 | 355215000 | 0.028 | — | 7.023 | SOLVENT PEAK | — | <min rt | | | |
| 1.663 | 987 | 0.023 | — | 7.401 | — | — | <min rt | | | |
| 3.872 | 1386 | 0.026 | 1.123 | 11.608 | 12:0 ISO | 1.91 | *deviates | −0.000 | Ref | 0.003 |
| 4.188 | 462 | 0.029 | 1.098 | 12.001 | 12:0 | 0.62 | *deviates | 0.000 | Ref | 0.003 |
| 4.816 | 7620 | 0.028 | 1.063 | 12.612 | 13:0 | 9.93 | *deviates | 0.000 | Ref | 0.002 |
| 4.907 | 1248 | 0.028 | 1.058 | 12.700 | 13:0 ANTEISO | 1.62 | *deviates | −0.000 | Ref | 0.002 |
| 5.981 | 6954 | 0.032 | 1.014 | 13.616 | 14:0 ISO | 8.64 | *deviates | −0.001 | Ref | 0.001 |
| 6.457 | 3522 | 0.036 | 0.997 | 14.000 | 14:0 | 4.31 | *deviates | −0.000 | Ref | 0.001 |
| 7.344 | 15144 | 0.034 | 0.974 | 14.621 | 15:0 ISO | 10.07 | *deviates | 0.001 | Ref | 0.002 |
| 7.472 | 3828 | 0.035 | 0.970 | 14.712 | 15:0 | 4.55 | *deviates | 0.001 | Ref | 0.002 |
| 7.884 | 630 | 0.037 | 0.961 | 15.000 | 15:0 | 0.74 | *deviates | 0.000 | Ref | 0.001 |
| 8.262 | 522 | 0.037 | — | 15.242 | — | — | | | | |
| 8.489 | 1770 | 0.037 | 0.948 | 15.386 | 16:1 w7c alcohol | 2.06 | *deviates | 0.000 | | |
| 8.638 | 2772 | 0.038 | 0.946 | 15.482 | Sum In Feature 3 | 3.21 | *deviates | −0.001 | 16:1 ISO I/14:0 30 | |
| 8.862 | 8508 | 0.041 | 0.941 | 15.624 | 16:0 ISO | 9.82 | *deviates | −0.002 | Ref | −0.001 |
| 9.071 | 642 | 0.045 | 0.938 | 15.758 | 16:0 w11c | 0.74 | *deviates | 0.001 | | |
| 9.225 | 8784 | 0.039 | 0.935 | 15.856 | Sun In Feature 4 | 10.07 | *deviates | 0.000 | 16:1 w7t/15i20H | |
| 9.451 | 6324 | 0.038 | 0.931 | 16.000 | 16:0 | 7.22 | *deviates | 0.000 | Ref | 0.001 |
| 9.806 | 756 | 0.040 | 0.926 | 16.215 | 15:0 20E | 0.86 | *deviates | −0.002 | | |
| 10.091 | 2874 | 0.039 | 0.922 | 16.387 | ISO 17:1 w10c | 3.25 | *deviates | 0.000 | | |
| 10.212 | 2370 | 0.045 | 0.920 | 16.460 | ISO 17:1 w5c | 2.67 | *deviates | −0.001 | | |
| 10.343 | 654 | 0.040 | 0.918 | 16.539 | 17:1 ANTEISO A | 0.74 | *deviates | −0.002 | | |
| 10.493 | 6180 | 0.040 | 0.916 | 16.630 | 17:0 ISO | 6.94 | *deviates | 0.001 | Ref | 0.002 |
| 10.644 | 1194 | 0.039 | 0.914 | 16.271 | 17:0 ANTEISO | 1.34 | *deviates | −0.001 | Ref | 0.000 |
| 12.806 | 648 | 0.038 | 0.889 | 18.000 | 18:0 | 0.71 | *deviates | −0.000 | Ref | 0.001 |
| ****** | 2772 | — | — | — | Summed Feature 3 | 3.21 | 12:0 ALDE? | | unknown 10.928 | |

TABLE 3-continued

Gas Chromatography of AQ52

| ****** | — | — | — | — | — | — | 16:1 ISO I/14:0 30H | 14:0 30H/16:1 ISO I |
| ****** | 8784 | — | — | — | Summed Feature 4 | 10.07 | 15:0 ISO 20H/16:1w7t | 16:1 w7t/15i20H |

| *ECL Solvent Ar | Total Area | Named Area | % Named | Total Amnt | Nbr Rev | ECL Deviation | Ref ECL Shift |
|---|---|---|---|---|---|---|---|
| 355215000 | 84792 | 84270 | 99.38 | 81581 | 14 | 0.001 | 0.002 |

| TSBA | [Rev 3.80)] | Bacillus | 0.159 | (*Bacillus cereus* group) |
| | | *B. thuringiensis* | 0.159 | (*Bacillus cereus* group) |
| | | *B. cereus* | 0.107 | |
| CLIN | [Rev 3.80] | *NO MATCH* | | |
| RHI %-1 | [Rev 1.0] | *NO MATCH* | | |

AQ52 Does Not Produce Beta-exotoxin

To determine if AQ52 produces beta-exotoxin, the following High Pressure Liquid Chromatography (HPLC) experiment was performed. A solid phase cartridge (ODS-4) was activated with 10 mL methanol and washed with 20 mL of 20 mM sodium phosphate (pH 4.0). A 2 mL sample of AQ52 was centrifuged at 12,000 rpm for 15 minutes, passed through a 0.2 $\mu$m filter and 1 mL loaded onto the activated cartridge. After washing the cartridge with 1 mL of 20 mM sodium phosphate, the material of interest was eluted with 4 mL of 30:70 methanol/sodium phosphate into a 5 mL volumetric flask. 100 $\mu$L of 0.4M tertbutyl ammonium hydroxide was added to the flask and the volume brought up to 5 mL with water. A 200 $\mu$L sample was injected onto a C18 HPLC colamn (4.6mm×25cm) using 45:55 methanol/tetrabutyl ammonium dihydrogen phosphate (pH 6.5) at a rate of 1 mL per minute. The UV spectrum at 254 nm was recorded for 15 minutes and compared with the UV spectrum of a known beta-exotoxin. No peaks were eluted from the AQ52 sample where beta-exotoxin normally appears. Thus, it was demonstrated that AQ52 does not produce beta-exotoxin.

AQ52 Produces Zwittermicin-A

Bacterial strains known to produce zwittermicin-A exhibit synergistic effects with *Bacillus thuringiensis*. (see, Manker et al. WO/9409630). Therefore, to determine whether AQ52 produces zwittermicin-A, cultures of selected strains were mixed with Javelin® (*B. thuringiensis*) and observed for synergistic activity. More specifically, 50 mL cultures of AQ52 and known zwittermicin-producing strains AQ 175 (ATC 55608) and AQ 177 (ATCC 55609) were grown in TSB for three days at 29° C. The whole broth cultures were centrifuged at 4,200 g for 20 minutes. The supernatants were decanted and stored at −20° C. One mL of each supernatant was used as a stock, while one mL was diluted with 500 μL of sterile distilled water. Eight serial dilutions were then made from the diluted sample.

Javelin® WG (0.0521 g) was mixed with 50 mL of distilled water to produce a 1000 μg/mL stock solution. The stock solution was then serially diluted in distilled water to give eight 0.5 mL solutions. A 50:50 mixture of the Javelin® stock solution and each supernatant stock solution were then serially diluted and then transferred to a 96-well microtiter plate. 40 μL aliquots of each dilution were dispensed into the wells of a microtiter plate containing 200 μL/well of artificial diet. The samples were dried at room temperature and 5–10 synchronized beet armyworm eggs suspended in 25 μL of a 1% agar were added, to each well. The egg agar was allowed to dry, and the plates covered with perforated Mylar®. After seven days, the number of live insects in each sample well was tabulated. Results are shown in Table 4.

TABLE 4

AQ52 Enhancement of Javelin. Number of Living Insects

| | Javelin ® concentration (μg) | | | | | | | |
|---|---|---|---|---|---|---|---|---|
| | 43 | 29 | 19 | 13 | 9 | 6 | 4 | 3 |
| Javelin alone (#1) | 2 | 2 | 2 | 9 | 8 | 12 | 4 | 8 |
| Javelin alone (#2) | 1 | 5 | 6 | 7 | 4 | 8 | 7 | 7 |
| Jav + AQ52 | 0 | 2 | 1 | 4 | 6 | 18 | 13 | 10 |
| AQ52 alone | 15 | 15 | 15 | 14 | 8 | 13 | 13 | 10 |

| | Javelin ® concentration (μg) | | | | | | | | |
|---|---|---|---|---|---|---|---|---|---|
| | 41.6 | 27.4 | 18.1 | 12 | 7.9 | 5.2 | 3.4 | 2.3 | 1.5 |
| Javelin alone (#1) | 1s[a] | 1s | 3s | 5s | 11 | 14 | 13 | 22 | nd |
| Javelin alone (#2) | 1s | 2s | 3s | 6s | 17 | 22 | 19 | 17 | nd |
| Jav + AQ175 | nd | 0 | 0 | 0 | 0 | 0 | 2s | 5s | 14 |
| Jav + AQ177 | nd | 0 | 0 | 0 | 0 | 0 | 4s | 9s | 18 |

[a]The "s" indicates that the living insects were extremely stunted compared to controls.
nd = not done.

The results show that AQ52 supernatant does not, by itself, inhibit growth of beet armyworms. However, when AQ52 supernatant is combined with *B. thuringiensis*, Javelin®, the synergistic effect characteristic of zwittermicin is seen as with known zwittermicin-producing strains AQ175 and AQ177. Thus, AQ52 produces a zwittermicin-like antibiotic in its supernatant.

Example 2

Activity of AQ52 in In-vitro Culture

To determine if AQ52 is effective against the fungi, *Phytophthora infestans, Pythium ultimum, Botrytis cinerea, Rhizoctonia solani, Alternaria solani,* the following experiments were performed. 96-well plates (flatbottomed, 400 microliters per well, Nunc brand) were filled with an agar medium (potato dextrose agar (PDA), Difco). *Phytophthora infestans* cultures were grown for three days in liquid YPG-1 medium (0.4 g yeast extract, 0.1% $KH_2PO$, 0.5% $MgSO_4 \times 7H_2O$, 1.5% glucose). For the other fungi, spores were scraped from the surface of petri plates and 0.1–0.2 mLs aliquots of deionized water and spore suspension (concentration approximately $2\times10^6$ spores/mL) of pathogen were spread onto the agar.

AQ52 was grown for three to five days in a cottonseed extract medium (proflo, dextrose, peptone, Trader's Protein). To test whole broth cultures, the strain was grown to approximately $9.0\times10^8$ and aliquots were taken from these cultures. Supernatant was obtained by density centrifugation of the culture it 5,200 rpm for 20 minutes.

The fungal plant pathogen suspensions were pipetted onto the PDA into the 96-well plates (8 wells per pathogen). The presence or absence of fungal growth was recorded for each of 8 wells. Approximately 40 μL of AQ52 supernatant was then added to each well. A score of "1" means complete inhibition of fungal growth. A score of "4" means no inhibition of fungal growth. Results are shown in Table 5.

TABLE 5

AQ52 Inhibition of Fungal Growth

| | Phytophthora | Pythium | Botrytis | Rhizoctomia | Alternaria |
|---|---|---|---|---|---|
| AQ52 Supernatant | 1 | 1 | 1 | 4 | 1 |

A zone inhibition test was carried out also. Fungal strains were grown and prepared as before. Petri plates were filled with PDA medium. Two 7 mm holes were made in each petri dish. A volume of 100 μL of test sample (either supernatant or whole broth) was added to each 7 mm hole. Each test was performed in duplicate. No bacterial test sample was added to the control plate. The zone of inhibition, measured in millimeters (mm) around each hole as measured 3 to 10 days. Results for the Phytophthora, Botrytis, Rhizoctonia, Alternaria, Pythium are shown in Table 5. Results are shown for supernatant (su) and whole broth (wb) in Table 6.

TABLE 6

Zone Inhibition of Fungi by AQ52 Supernatant or Whole Broth

| | Phytophthora | Pythium | Botrytis | Alternaria |
|---|---|---|---|---|
| AQ52su | 10 mm | 11 mm | 13 mm | Not tested |
| AQ52wb | 15 | 10 | 16 | 18 mm |

The same experiment was repeated to test AQ52 against the fungus *Trichoderma harzianum*, an important pathogen of mushrooms. *Trichoderma harzianum*, strain T-14, was obtained from Campbell (Davis Calif.). A sterile number four cork borer was used to make four wells in PDA plates. AQ52 was applied to one of the four wells. Two discs of number four cork borer-sized Trichoderma mycelial plugs were added to each plate in between two wells in each side of the plate. Results were recorded 24 hours later. The size of the cleared zone between the bacterium and the mycelium was recorded. AQ52 gave a 1 mm zone from the edge of the well.

To determine in vitro effectiveness of these strains against the fungi *Erwinia herbicola* and *Monilinia fructicola*., the following experiment was conducted. Bacterial strains were cultured as described above. *Monilinia fructicola* cultures were grown on V-8 agar (20 g agar, 4 g CaCO₃, 200 mL V-8 juice) in the dark at room temperature for 8 days. Spores were harvested by placing sterile distilled water on the surface of the culture plates and scraping the surface with a sterile needle to dislodge the spores. Spore concentration was adjusted to $3.3 \times 10^6$ spores/mL and 400 μl added to 4 mL of soft potato dextrose agar. This mixture was poured over the surface of potato dextrose agar culture places and the soft agar allowed to solidify. Erwinia herbicola was fermented overnight in half-strength TSA and $1 \times 10^5$ cells were mixed with soft molten agar and poured into a petri plate. Using a sterile no. 4 cork borer, 5 welts were 5 made in each plate and 100 μL of a three day old culture of AQ52 was added to each well. Plates were incubated at room temperature in the dark and the zones of no growth of the around each well measured. Results are summarized in Table 7.

TABLE 7

Bacterial inhibition of M. fructicola and E. herbicola

| | M. fructicola | Plate 1 E. herbicola | Plate 2 E. herbicola |
|---|---|---|---|
| AQ52 | 11 mm | 9 mm | 11 mm |
| Water | 0 | 0 | 0 |

These results demonstrate that AQ52 inhibited growth of M fructicola, and also inhibited E. herbicola growth.

Example 3
Antibiotic Activity Using Whole Plants

The ability of AQ52 to control late blight (*P. infestans*) infection was tested on whole tomato plants. Tomato plants (Ace and Patio varieties) were, purchased from Ace hardware. Bacterial strain AQ52 was grown to $9 \times 10^8$ CFU/mL in a cotton seed extract medium (peptone, dextrose, yeast, soy and proflo, Trader's Protein) for three days. *P. infestans* cultures were prepared is described in Example 2. Three tomato plants (1 pack) were sprayed to runoff with a whole broth culture or supernatant of AQ52, and then air-dried at approximately 70° F. Three control plants were untreated. All plants were then sprayed to runoff with a *P. infestans* culture at $1.55 \times 10^5$ CFU/mL. The plants were air-dried at 70° F., lightly misted with de-ionized water, enclosed in a clear plastic bag and incubated at approximately 16° C. The amount of late blight infestation and bacterial speck (*Pseudomonas syringae*) which occurred naturally on the tomatoes was recorded fifteen days after treatment. Results are shown in Table 8.

TABLE 8

Late blight and bacterial speck infection fifteen days after treatment with AQ52

| Bacterial strain - Tomato Plant Ace (A) Patio (P) | Whole Broth or Supernatant | # infected leaves/# of leaves | Percent Infection | Bacterial Speck Infection |
|---|---|---|---|---|
| AQ 52 (A) | supernatant | 1\34 | 2.9 | No |
| AQ52 (P) | supernatant | 0\29 | 0.0 | Bacterial Speck |
| Average | | | 1.5 | |
| AQ52 (A) | whole broth | 1\37 | 2.7 | |
| AQ52 (P) | whole broth | 5\32 | 15.6 | |
| Average | | | 9.2 | |
| Phytophthora untreated control | | | | 100% covered with speck |
| (A) | | 6\26 | 23.1 | Full of bacterial speck |
| (P) | | 4\32 | 12.5 | Full of bacterial speck |
| Average | | | 17.8 | |

These results show that the whole broth or supernatant of AQ52 is effective against late blight and bacterial speck.

Example 4
Antibiotic Activity of AQ52 Against *B. Cinerea*

To test the effectiveness of the antibiotic-producing bacterial strains of the present invention against *B. cinerea*, fresh strawberries picked the day of testing were utilized. AQ52 supernatants were obtained from strains grown in either proflo medium or in TSB. Whole broth cultures and supernatants were sprayed onto the strawberries until runoff, then allowed to air dry.

*B. cinerea* spores were grown on potato dextrose agar in a petri plate and scraped into de-ionized water to form a liquid inoculum. The *B. cinerea* inoculum, measuring approximately $5.8 \times 10^5$ cells per mL was sprayed onto the berries until runoff, and the berries allowed to air dry. All berries were placed uncovered in an incubator at approximately 16° C. Results are shown in Table 9.

TABLE 9

AQ52 Inhibition of *B. cinerea*

| Botrytis test Bacterial strain | No. Strawberries per treatment | # infected/# clean |
|---|---|---|
| 52(proflo) whole broth | 2 | 0/2 |
| 52(proflo) supernatant | 2 | 1/1 |
| 52(TSB) whole broth | 2 | 0/2 |
| 52(TSB) supernatant | 2 | 1/1 |
| Untreated control | 2 | 1/1 |

Whole broth cultures of AQ52 was completely effective at preventing *B. cinerea* infection, regardless of the medium used.

Example 5
Antibiotic Activity of AQ52 Against a Spectrum of Fungal Pathogens

To test the AQ52 strain against a number of fungal pathogens, AQ52 was grown in cottonseed extract media. Cells were cultured to $9.0 \times 10^8$ cells/mL. Replicates of three test plants and three control plants per pathogen were utilized. The test plants were each sprayed with a whole broth culture of a antibiotic-producing bacterial strain to run-off with a hand-held sprayer. When the foliage had dried, each test plant was sprayed a second time. After the second application of the bacterial strain culture has dried, the test plants and the control plants were inoculated with the appropriate fungal pathogen. Plants were incubated under conditions conducive to disease development. In addition, positive controls were utilized by testing known pesticides against appropriate fungal pathogens in the same manner as the cultures of the bacterial strains were tested. Each plant was evaluated by estimating the percent disease control using a scale from 0% control to 100% control. (0=disease level of untreated control; 100=plants with no visible lesions). The fungal pathogens, resulting diseases, host plant and control pesticides are presented in Table 10. The results are shown in Table 11.

TABLE 10

| Disease | Pathogen | Host Plant | Standard Pesticide |
|---|---|---|---|
| Late Blight | *Phytophthora infestans* | tomato | metalaxyl |
| Early Blight | *Alternaria solani* | tomato | propiconazole |
| Gray Mold | *Botrytis cinerea* | pepper | propiconazole |
| Downy Mildew | *Plasmopara viticola* | grape | metalaxyl |
| Powdery Mildew | *Unicinula necator* | grape | propiconazole |
| Leaf Rust | *Puccinia recondita* f.sp. *tritici* | wheat | propiconazole |
| Glume Blotch | *Staganospora nodorum* | wheat | propiconazole |

TABLE 11

| Treatment | Rate (ppm) | % disease control | | | | | | |
|---|---|---|---|---|---|---|---|---|
| | | Pi[y] | As | Pv | Un | Bc | Sn | Pr |
| AQ52 | — | 0 | 0 | 98 | 53 | 100 | 0 | 87 |
| metalaxyl | 30 | 90 | — | 100 | — | — | — | — |
| | 20 | — | — | 67 | — | — | — | — |

TABLE 11-continued

| Treatment | Rate (ppm) | % disease control | | | | | | |
|---|---|---|---|---|---|---|---|---|
| | | Pi[y] | As | Pv | Un | Bc | Sn | Pr |
| | 10 | 47 | — | — | — | — | — | — |
| myclobutanil | 10 | — | — | — | 100 | — | — | — |
| | 1 | — | — | — | 0 | — | — | — |
| propiconazole | 250 | — | 93 | — | — | — | — | — |
| | 30 | — | 37 | — | — | — | — | — |
| | 10 | — | — | — | — | 100 | 100 | — |
| | 5 | — | — | — | — | 63 | 73 | 95 |
| | 1 | — | — | — | — | — | — | 33 |
| Disease Index (%)[Z] | — | 50 | 80 | 75 | 30 | 80 | 80 | 80 |

[y]Pi = *P. infestans*, As = *A. solani*, Pv = *P. viticola*, Un = *U. necator*, Bc = *B. cinerea*, Sn = *S. nodorum*, Pr = *P. recondita* f.sp. *tritici*.
[Z]Disease index = percent diseased tissue on the untreated, inoculated plants.

AQ52 provide complete control of B. cinerea and nearly complete control of P. viticola, grape downy mildew. It also has activity against rust and powdery mildew.

Example 6
Activity of AQ52 Versus Brown Rot, *Monilinia fructicola* on Peach Fruit 250 mLs cultures of AQ52 were grown in cottonseed extract medium as previously described grown for 3.5 days. Peaches were surface sterilized with 10% Clorox solution, rinsed with deionized water and air dried. Whole fermentation broths of AQ52 ($7 \times 10^5$ CFU/mLs) were sprayed with a hand held sprayer on two peaches until runoff (approximately 50 mLs per two peaches). The peaches were allowed to air dry. Monilinia spores were scraped from a petri plate and suspended in deionized water to at $1.09 \times 10^5$ cells per mL. The peaches were sprayed with the spore suspension until runoff and allowed to air dry. Two peaches were untreated and two peaches were sprayed with Monilinia, but with no treatments. The peaches were placed in a polypropylene container in an incubator in the dark at 18° C. Four and six days later the amount of brown rot was recorded. The following results were recorded:

TABLE 12

AQ52 Inhibition of *M. fructicola*

| | Four days | Six days |
|---|---|---|
| AQ52 peach 1 | 2.5 × 2.25 cm lesion | 10 × 5 cm lesion |
| AQ52 peach 2 | No infection | 4 × 3 cm lesion |
| Untreated peach 1 | 9 × 7 cm lesion | 11 × 7 cm lesion |
| Untreated peach 2 | 3 × 2 cm lesion | 11 × 12 cm lesion |
| Monilinia only peach 1 | 7 × 5 cm lesion | 10 × 10 cm lesion |
| Monilinia only peach 2 | 4 × 3 cm lesion | 10 × 6 cm lesion |

The results show that AQ52 suppressed Monilinia brown rot on peaches compared to the untreated controls and Monilinia only peaches. The treatments at 4 days had only one peach with brown rot the size of the lesions was much smaller than the untreated and Monilinia controls. At six days, the peaches were all heavily infected with brown rot, but the size of the lesions in the AQ52 treatment was still smaller than in the untreated or Monilinia only controls.

Having now fully described this invention, it will be appreciated by those skilled in the art that the same can be performed within a wide range of equivalent parameters, concentrations and conditions without departing from the spirit and scope of the invention and without undue experimentation. While this invention has been described in connection with specific embodiments thereof, it will be under- stood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows the scope of the appended claims.

What is claimed is:

1. An isolated, pure culture of *Bacillus thuringiensis* strain AQ52, NRRL Accession No. B-21619 and mutants thereof, said pure culture and mutants having pesticidal activity against fungal or bacterial infections.

2. A method for protecting or treating fungal or bacterial infections in plants and fruits comprising applying an effective amount of the *Bacillus thuringiensis* strain of claim 1.

3. The method of claim 2 wherein the infections are caused by at least one of microorganism of the group consisting of *Phytopthora infestans, Botrytis cinerea, Uncinula necator, Puccinia recondita, Plasmopara viticola, Erwinia herbicola, Monilinia fructicola, Alternaria solani, Pseudomonas syringae* and *Trichoderma harzianum*.

4. A composition comprising the strain of claim 1 and a carrier.

5. The composition of claim 4, wherein the composition is formulated as a whole broth culture.

6. The composition of claim 4, wherein the composition is formulated as a wettable powder, a granules, a flowable, or as a microencapsulated formulation.

7. The composition of any one of claims 4, 5 or 6 further comprising at least one chemical pesticide.

8. The composition of any one of claim 4, 5 or 6 further comprising at least one biological pesticide.

9. A composition comprising the supernatant isolated from the strain of claim 1 and a carrier.

10. The composition of claim 9, wherein the strain is *Bacillus thuringiensis* strain AQ52, NRRL Accession No. B-21619.

11. The composition of claim 9 or 10, wherein the composition is formulated as a whole broth culture.

12. The composition of claim 9 or 10, wherein the composition is formulated as a wettable powder, a granule, flowable or in a microencapsulated formulation.

13. The composition of claims 9 or 10, further comprising at least one chemical pesticide.

14. The composition of claim 13, wherein the composition is formulated as a wettable powder, a granule, flowable or microencapsulated formulation.

15. The composition of claims 9 or 10, further comprising at least one biological pesticide.

16. The composition of claim 15, wherein the composition is formulated as a wettable powder, a granule, flowable or microencapsulated formulation.

17. A method for protecting or treating fungal or bacterial infections in plants or fruits comprising applying an effective amount of the *Bacillus thuringiensis* strain of claim 1.

18. A method for protecting or treating fungal or bacterial infections in plants or fruits comprising applying an effective amount of any one of the compositions of claims 4, 5, 6 or 10 to the plants or fruits.

19. A method for protecting or treating fungal or bacterial infections in plants or fruits comprising applying an effective amount of the composition of claim 13 to the plants or fruits.

20. A method for protecting or treating fungal or bacterial infections in plants or fruits comprising applying an effective amount of the composition of claim 15 to the plants or fruits.

21. The supernatant obtained from the culture of claim 1.

* * * * *

UNITED STATES PATENT AND TRADEMARK OFFICE
CERTIFICATE OF CORRECTION

PATENT NO. : 6,077,506
DATED : June 20, 2000
INVENTOR(S) : Pamela G. Marrone, Sherry D. Heins, Denise C. Manker, Desmond R. Jiménez, Chris N. Chilcott, Peter Wigley and Andrew Broadwell It is certified that error appears in the above-identified patent and that said Letters Patent is hereby corrected as shown below:

On the cover sheet, second column, line 20, replace "Aademic Press, San Diego" with -- Academic Press, San Diego --.

Column 15, line 17, replace "arc" with -- are --.

Signed and Sealed this

First Day of May, 2001

Attest:

NICHOLAS P. GODICI

Attesting Officer     *Acting Director of the United States Patent and Trademark Office*